US009002077B2

(12) United States Patent
Hoyt et al.

(10) Patent No.: US 9,002,077 B2
(45) Date of Patent: Apr. 7, 2015

(54) VISUALIZATION OF STAINED SAMPLES

(75) Inventors: Clifford C. Hoyt, Wellesley, MA (US); Richard Levenson, Brighton, MA (US)

(73) Assignee: Cambridge Research & Instrumentation, Inc., Hopkinton, MA (US)

( * ) Notice: Subject to any disclaimer, the term of this patent is extended or adjusted under 35 U.S.C. 154(b) by 938 days.

(21) Appl. No.: 12/854,058

(22) Filed: Aug. 10, 2010

(65) Prior Publication Data

US 2011/0182490 A1    Jul. 28, 2011

Related U.S. Application Data

(60) Provisional application No. 61/232,613, filed on Aug. 10, 2009.

(51) Int. Cl.
*G06K 9/00* (2006.01)
*G06T 7/00* (2006.01)
*G01N 1/30* (2006.01)
*G06K 9/46* (2006.01)

(52) U.S. Cl.
CPC .......... *G06K 9/00147* (2013.01); *G06T 7/0081* (2013.01); *G06T 7/0097* (2013.01); *G01N 1/30* (2013.01); *G06K 2009/00644* (2013.01); *G06K 2009/4657* (2013.01); *G06T 2207/10152* (2013.01); *G06T 2207/30024* (2013.01)

(58) Field of Classification Search
None
See application file for complete search history.

(56) References Cited

U.S. PATENT DOCUMENTS

| 5,521,705 | A  | 5/1996  | Oldenbourg et al. |
| 5,539,517 | A  | 7/1996  | Cabib et al. |
| 5,784,162 | A  | 7/1998  | Cabib et al. |
| 5,991,028 | A  | 11/1999 | Cabib et al. |
| 5,995,645 | A  | 11/1999 | Soenkson et al. |
| 6,007,996 | A  | 12/1999 | McNamara et al. |
| 6,142,629 | A  | 11/2000 | Adel et al. |
| 6,195,451 | B1 | 2/2001  | Kerschmann et al. |
| 6,373,568 | B1 | 4/2002  | Miller et al. |
| 6,421,131 | B1 | 7/2002  | Miller |
| 6,690,466 | B2 | 2/2004  | Miller et al. |
| 6,920,239 | B2 | 7/2005  | Douglass et al. |
| 6,924,893 | B2 | 8/2005  | Oldenbourg et al. |
| 2003/0081204 | A1 | 5/2003  | Cronin et al. |
| 2003/0138140 | A1 | 7/2003  | Marcelpoil et al. |
| 2003/0223248 | A1 | 12/2003 | Cronin et al. |
| 2005/0065440 | A1 | 3/2005  | Levenson |

(Continued)

FOREIGN PATENT DOCUMENTS

| WO | WO 98/43042    | 10/1998 |
| WO | WO 2005/040769 | 5/2005  |

(Continued)

*Primary Examiner* — Robert Morgan
*Assistant Examiner* — Michael Tomaszewski
(74) *Attorney, Agent, or Firm* — Fish & Richardson P.C.

(57) ABSTRACT

Methods and systems are disclosed that include: applying an immunohistochemical stain, eosin, and a counterstain to a sample; obtaining a plurality of images of the sample, each of the plurality of images corresponding to radiation from the sample in a different wavelength band; decomposing the plurality of images of the sample to obtain component images corresponding to the immunohistochemical stain, eosin, and the counterstain; and generating a sample image based on the component images, where the sample image includes contributions from the counterstain and from one of the immunohistochemical stain and eosin, and substantially not from the other of the immunohistochemical stain and eosin.

31 Claims, 1 Drawing Sheet

(56) References Cited

U.S. PATENT DOCUMENTS

| | | |
|---|---|---|
| 2006/0082762 A1 | 4/2006 | Leverette et al. |
| 2006/0119865 A1 | 6/2006 | Hoyt et al. |
| 2006/0245631 A1 | 11/2006 | Levenson et al. |
| 2007/0016082 A1 | 1/2007 | Levenson et al. |
| 2007/0231784 A1 | 10/2007 | Hoyt et al. |
| 2008/0074644 A1* | 3/2008 | Levenson et al. ............... 356/36 |
| 2008/0074649 A1* | 3/2008 | Levenson et al. ............... 356/73 |
| 2009/0226059 A1 | 9/2009 | Levenson et al. |
| 2009/0257640 A1 | 10/2009 | Gossage et al. |
| 2010/0075373 A1 | 3/2010 | Hoyt |
| 2011/0182490 A1 | 7/2011 | Hoyt et al. |

FOREIGN PATENT DOCUMENTS

| | | |
|---|---|---|
| WO | WO 2006/081547 | 8/2006 |
| WO | WO 2008/039758 | 4/2008 |

\* cited by examiner

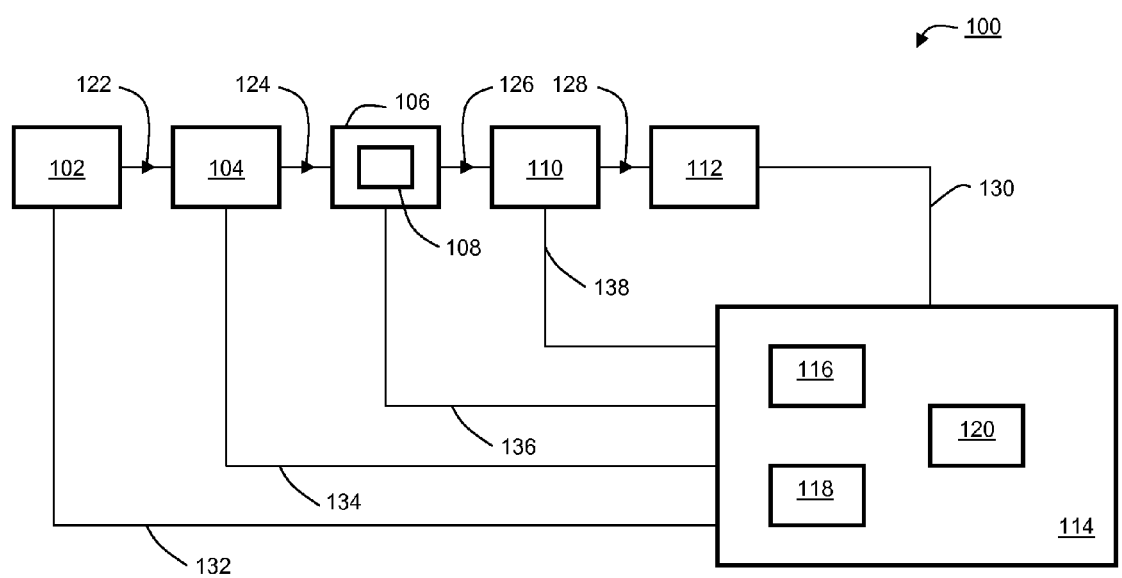

VISUALIZATION OF STAINED SAMPLES

CROSS-REFERENCE TO RELATED APPLICATIONS

This application claims priority to U.S. Provisional Application Ser. No. 61/232,613, filed on Aug. 10, 2009, the entire contents of which are incorporated by reference herein.

TECHNICAL FIELD

This disclosure relates to biological sample imaging and analysis.

BACKGROUND

A common goal in automated image analysis of stained tissue sections is to measure the amount of an indicator stain that indicates some property or state of tissues or cells of interest. This typically involves finding segmentation regions corresponding to the tissue of interest in images of tissue sections, or finding certain types of cells, or finding subcellular compartments of cells of interest; and then assessing levels of indicator stains from pixels within these segmented regions.

SUMMARY

In general, in a first aspect, the disclosure features a method that includes: applying an immunohistochemical stain, eosin, and a counterstain to a sample; obtaining a plurality of images of the sample, each of the plurality of images corresponding to radiation from the sample in a different wavelength band; decomposing the plurality of images of the sample to obtain component images corresponding to the immunohistochemical stain, eosin, and the counterstain; and generating a sample image based on the component images, where the sample image includes contributions from the counterstain and from one of the immunohistochemical stain and eosin, and substantially not from the other of the immunohistochemical stain and eosin.

Embodiments of the method can include one or more of the following features.

The decomposing can include spectral unmixing. The counterstain can include hematoxylin. The method can include converting intensity values in each of the plurality of images into measurements of optical density.

The sample image can include contributions from the immunohistochemical stain and the counterstain, and substantially not from eosin. The sample image can include contributions from eosin and the counterstain, and substantially not from the immunohistochemical stain.

The sample image can include contributions from substantially only the immunohistochemical stain and the counterstain, and the method can further include generating a second sample image, where the second sample image includes contributions from substantially only eosin and the counterstain.

The immunohistochemical stain can correspond to a first immunohistochemical stain, and the method can include applying a second immunohistochemical stain to the sample, where the decomposing includes obtaining a component image corresponding to the second immunohistochemical stain. The method can include generating a second sample image based on the component images, where the second sample image includes contributions from the counterstain and one of the first immunohistochemical stain, the second immunohistochemical stain, and eosin, and substantially not from the others of the first immunohistochemical stain, the second immunohistochemical stain, and eosin.

Embodiments of the method can also include any of the other features or method steps disclosed herein, as appropriate.

In another aspect, the disclosure features a method that includes applying an immunohistochemical stain, eosin, and a counterstain to a sample, obtaining a plurality of images of the sample, each of the plurality of images corresponding to radiation from the sample in a different wavelength band, and using an electronic processor to: (i) decompose the plurality of images of the sample to obtain component images corresponding to the immunohistochemical stain, eosin, and the counterstain; (ii) analyze one or more of the component images to identify one or more regions of interest in the sample; (iii) determine an amount of the immunohistochemical stain in one or more of the regions of interest; and (iv) output one or more indicators corresponding to the determined amount of the immunohistochemical stain.

Embodiments of the method can include any one or more of the following features.

The method can include generating one or more component images each including a measure of optical density associated with at least one of the immunohistochemical stain, eosin, and the counterstain. The decomposing can include spectral unmixing. The counterstain can include hematoxylin.

The method can include generating a sample image based on the component images, where the sample image includes contributions from the counterstain and from one of the immunohistochemical stain and eosin, and substantially not from the other of the immunohistochemical stain and eosin. The sample image can include contributions from the immunohistochemical stain and the counterstain, and substantially not from eosin. The sample image can include contributions from eosin and the counterstain, and substantially not from the immunohistochemical stain.

The sample image can include an indicator based on the determined amount of the immunohistochemical stain. The indicator can correspond to a measurement of abundance of the immunohistochemical stain in the sample.

Regions of interest in the sample can be identified based on at least a component image corresponding to eosin. Alternatively, or in addition, the regions of interest in the sample can be identified based on at least a component image corresponding to the counterstain.

Embodiments of the method can also include any of the other features or method steps disclosed herein, as appropriate.

In a further aspect, the disclosure features a method that includes: applying an immunohistochemical stain, eosin, and a counterstain to a sample; obtaining a plurality of images of the sample, each of the plurality of images corresponding to radiation from the sample in a different wavelength band; decomposing the plurality of images of the sample to obtain component images corresponding to the immunohistochemical stain, eosin, and the counterstain; and generating a sample image based on the eosin and counterstain component images, where the sample image includes an indicator based on information derived from the immunohistochemical component image.

Embodiments of the method can include any one or more of the following features.

The indicator can include markers identifying the presence of the immunohistochemical stain in regions of the sample image. The indicator can include markers identifying regions of the sample image where an amount of the immunohistochemical stain exceeds a predetermined non-zero threshold amount. The indicator can include markers identifying regions of the sample image where an optical density of the immunohistochemical stain is larger than a predetermined non-zero optical density.

The decomposing can include spectral unmixing. The counterstain can include hematoxylin.

Embodiments of the method can also include any of the other features and method steps disclosed herein, as appropriate.

In another aspect, the disclosure features a system that includes: a source configured to direct radiation to a sample that includes an immunohistochemical stain, eosin, and a counterstain, a detector configured to measure radiation emitted from the sample to obtain a plurality of images of the sample, where each of the plurality of images corresponds to radiation from the sample in a different wavelength band, and an electronic processor configured to: (i) decompose the plurality of images of the sample to obtain component images corresponding to the immunohistochemical stain, eosin, and the counterstain; and (ii) generate a sample image based on the component images, where the sample image includes contributions from the counterstain and from one of the immunohistochemical stain and eosin, and substantially not from the other of the immunohistochemical stain and eosin.

Embodiments of the system can include any one or more of the following features.

The electronic processor can be configured to decompose the plurality of images of the sample by spectrally unmixing the images.

Embodiments of the system can also include any of the other features disclosed herein, as appropriate.

In a further aspect, the disclosure features a system that includes a source configured to direct radiation to a sample that includes an immunohistochemical stain, eosin, and a counterstain, a detector configured to measure radiation emitted from the sample to obtain a plurality of images of the sample, where each of the plurality of images corresponds to radiation from the sample in a different wavelength band, and an electronic processor configured to: (i) decompose the plurality of images of the sample to obtain component images corresponding to the immunohistochemical stain, eosin, and the counterstain; (ii) analyze one or more of the component images to identify one or more regions of interest in the sample; (iii) determine an amount of the immunohistochemical stain in one or more of the regions of interest; and (iv) output one or more indicators corresponding to the determined amount of the immunohistochemical stain.

Embodiments of the system can include any one or more of the following features.

The electronic processor can be configured to decompose the plurality of images of the sample by spectrally unmixing the images. The electronic processor can be configured to generate a sample image based on the component images, where the sample image includes contributions from the counterstain and from one of the immunohistochemical stain and eosin, and substantially not from the other of the immunohistochemical stain and eosin.

The sample image can include an indicator based on the determined amount of the immunohistochemical stain.

The electronic processor can be configured to identify the regions of interest in the sample based on at least a component image corresponding to eosin. The electronic processor can be configured to identify the regions of interest in the sample based on at least a component image corresponding to the counterstain.

Embodiments of the system can also include any of the other features disclosed herein, as appropriate.

Unless otherwise defined, all technical and scientific terms used herein have the same meaning as commonly understood by one of ordinary skill in the art to which this disclosure belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

FIG. 1 is a schematic diagram showing a system configured to acquire and process sample images.

DETAILED DESCRIPTION

To avoid sample bias, it can be desirable to segment regions of biological samples in a way that is unaffected by whether an indicator stain is present in a given tissue region, cell, or cell compartment. Moreover, it can often be advantageous to identify segmentation regions automatically or semi-automatically, so that data can be extracted from pixels in these regions, with little to no user input or intervention.

One technique for identifying target regions of interest is to use immunohistochemical (IHC) agents that are specific to these regions, and that bind to the target regions regardless of whether there is a indicator stain present or not. For example, it is believed that the AQUA® technology, available from HistoRX (New Haven, Conn.) uses this approach. These IHC stains have a molecular specificity so that regions of interest are delineated with high contrast. When such a stain is present in a sample, regions of interest in images of the sample can be identified using image analysis algorithms, including thresholding. Indicator stains can then be quantified within the regions thus delineated.

This approach uses some of the limited multiplexing bandwidth of microscopy staining methods to find the regions of interest. Bandwidth is limited by, among other things, biochemistry (e.g., how many different markers one can stain a sample with, without losing specificity to analytes), and by the number of stains that can be imaged without undue spectral crosstalk. Typically, these issues limit the number of specific markers to two or three in chromogenic applications, and four or five in fluorescence applications. As an example, if a fluorescence detection channel is dedicated to marking regions or objects of interest rather than indicating a molecular expression, then fewer channels remain for molecular marker analysis purposes.

It can be difficult to prepare stains that target regions of interest with the desired degree of specificity. As a result, many stains bind only imperfectly to sample regions of interest, and have limited generality. As an example, cytokeratin is typically used to find cytoplasm in breast cancer cells. However, there are no cytokeratins that uniformly stain all breast cancer tissues. One often has to choose from a long list of cytokeratins (~20), based on the specific tissue samples at hand.

More generally-applicable region-specific stains (and/or methods for using existing stains in a more general manner) would be useful in many applications. For example, a universal membrane stain for breast cancer would be very useful in Her2 testing. It would be desirable to quantify the percent of membrane area where the indicator stain was present, on a per cell basis, using image analysis algorithms. In this setting, a universal membrane-targeting stain would indicate all membrane pixels, and so would provide the denominator in this calculation. While some markers can be used for specific cases, the limited generality of existing markers limits the utility of this approach.

One approach to developing algorithms that find and segment target regions of interest is based on machine learning, neural networks, vector support machines, or other machine vision techniques. In this "learn-by-example" approach, an expert such as a trained pathologist manually indicates to the software what areas correspond to target regions or collections of pixels. There may be several region types corresponding to several types of tissue, or several target structures. The computer then develops an algorithm that correctly assigns tissue to the desired category based on the training examples.

The inForm® software package (available from Cambridge Research & Instrumentation, Woburn, Mass.) uses this approach. The inForm® software can be used to develop robust image analysis algorithms to find regions of interest in samples. It can distinguish between cancer tissue and stroma or inflammation; it can segment cell compartments such as cytoplasm, and nuclei; and all of this can be achieved without use of IHC agents to delineate regions of interest in a sample. For example, inForm® achieves reliable segmentation of tissue regions and cell compartments on images of samples prepared using conventional histology stains such as the combination of hematoxylin and eosin (H&E). This preparation also provides contextual information to a viewer such as a histotechnician or pathologist, who is trained to recognize cell structures and tissue structures in samples prepared this way.

Conventional IHC techniques typically do not involve applying H&E to the sample. This is probably because the commonly-used IHC stains are brown or red, and are hard to discern visually from the pink-colored eosin. As a result, in samples stained both with IHC stains and eosin, a human operator finds that the IHC stains adds clutter, and visually obscure information about localization of eosin. Conversely, eosin visually obscures information about localization of the IHC stains. The most common IHC combination is hematoxylin and DAB, and hematoxylin plus Vector red is common as well. Some companies offer multicolor staining products that use hematoxylin and combinations of two or more absorptive stains. These can be DAB, red, green, pink, purple, black, etc. For example, Vector Laboratories (Peterborough, England) supplies a variety of reagents including Vector Red, Vector Blue, NovaRED, Vector Black, Vector VIP, Vector SG, and Vector AEC. Generally, however, eosin is not applied to samples that as part of IHC processing, likely because doing so would make it harder for a pathologist to determine the amount and location of IHC stain present in regions of the sample due to the spectral interference between eosin and various IHC stains.

As a result, IHC analysis is typically performed using two or more tissue sections taken serially from the same tissue sample. For example, two serial tissue sections can be used for analysis; one section is prepared with H&E, and the other section is prepared with the IHC stain plus a hematoxylin (IHC&H). Pathologists often assess the H&E slide first to understand the tissue architecture, and then assess the IHC&H slide to understand the protein expression state of the tissue.

In one general aspect of the disclosure, machine learning-based, automated image segmentation algorithms have been found to be more effective when both a counterstain such as hematoxylin and eosin are present, rather than a counterstain alone. In another general aspect, automated analysis of tissue sections can be improved by inclusion of eosin with IHC stains that are applied to samples, such as using preparations of hematoxylin, eosin, and an IHC stain (H+E+IHC). Even though visual observation of the localization of IHC stains can be made more difficult by applying eosin to a sample, automated analysis of such samples can be improved by applying a combination of eosin and one or more IHC stains. In the following disclosure, reference is made to the use of hematoxylin in combination with eosin and one or more IHC stains. More generally, however, it is understood that the systems and methods disclosed herein can be used with a variety of counterstains including, but not limited to, hematoxylin. In general, any counterstain that binds to a sample and is useful for revealing tissue architectural features can be used. Contributions to the measured sample images from the counterstain can be determined, and a component image corresponding to the counterstain can be generated. Further, multiple counterstains can be applied to a sample to provide information about multiple different types of tissue architectural features.

In some embodiments, machine-based analysis includes taking several intensity images of the sample corresponding to several wavelength bands or color bands using a video camera or digital camera. The images are converted from measured intensity units to optical density units, and the optical density signals from the images are decomposed (e.g. spectrally unmixed) into contributions from, for example, hematoxylin, eosin, and each of the one or more individual IHC stains. The unmixed component signals (e.g. images) can be used as inputs to a machine learning classifier to segment tissue regions, cells, or cell compartments of interest, and image analysis approaches can be applied to the unmixed image associated with the IHC stain(s) to extract quantitative measures of IHC stain binding in the segmented region(s) of interest.

In certain embodiments, several IHC stains can be used on the same sample, each including a different chromogenic agent. Depending on the reagents involved, three or four IHC stains can be used successfully. Moreover, while present biochemical techniques make preparation of samples with greater numbers of IHC stains difficult, the systems and methods disclosed herein can be used with more than four IHC stains applied to a sample. Further, the methods and systems disclosed herein can be used when multiple counterstains are applied to samples.

In some embodiments, the multiple images of the sample correspond to multiple wavelength images acquired using a multispectral imaging system such as the Nuance® system (available from Cambridge Research & Instrumentation, Woburn Mass.). In certain embodiments, the multiple images correspond to the three primary-color images from an RGB camera, for example.

In a further general aspect of this disclosure, the unmixed component signals obtained by combinations of the spectrally unmixed components (H, E, or IHC) can be displayed on a display device such as a computer screen in various combinations of interest. For example, an operator can request a view that shows only the H and E components, with substantially no contribution from IHC stains, to provide a screen representation that is very similar to what one would see in the eyepieces of a microscope if the sample had been treated with H&E preparation. This enables the operator to see tissue context and architectural features.

The operator can also request an image that is formed from just the IHC and H components, with substantially no contribution from eosin, to provide a screen representation that is very similar to what one would see under a microscope if the sample had been treated with IHC&H preparation. This enables a visual assessment of the IHC stain binding. The operator may prefer to see the H&E view first and then view the IHC&H view; or may prefer to see them in the reverse order; or, the operator can alternate between the images if desired. When multiple IHC stains are present, each stain component can be shown separately, or contributions from multiple stains can be shown together. Images formed from component images corresponding to any one or more of the stains present in the sample can be generated and displayed at any time, according to what is desired by the operator.

By applying a combination of one or more IHC stains and eosin (and, in some embodiments, one or more additional stains such as hematoxylin) to a sample, all of the assessment and sample classification can be performed based on a single sample, rather than on serial tissue sections. That is, instead of treating two or more samples with different preparations, only one preparation is performed. Component images corresponding to the applied stains can be obtained from spectral images of the sample. Display images can correspond to some or all of the component images, and/or can be constructed from the component images automatically at the request of the system operator.

This aspect of the invention is especially valuable for samples that are inherently available in limited quantity or unique format, such as fine needle aspirates, or needle biopsies. With such samples, there is no ready way to use techniques such as that described earlier in connection with serial sections. The systems and methods disclosed herein provide for obtaining a full range of information from a single sample, including the architectural information (e.g., from an H&E image) along with the IHC information (e.g., from one or more IHC and counterstain views).

Even when a sample is present in a format and in sufficient quantity that serial sectioning is possible, such procedures can be burdensome and inconvenient. Analysis based on a single sample can eliminate the need to prepare and track paired samples. Also, since all display images are derived from the same parent images, the operator sees exactly the same sample in all cases, with no need to accommodate for differences or offsets between serial sections. The operator can switch readily between the two views, with perfect registration.

In a further general aspect, machine-based image analysis of samples prepared with H and E and IHC can be combined with visual assessment using one or more machine-generated images, where at least one component has been synthetically removed from at least one of the machine-generated images. In this manner, both automated and visual assessment of the same sample can be performed. For example, automated analysis techniques can be used while still providing for review and approval by a system operator, who is afforded preferred views for such review, such as a view of the sample as if prepared with only H&E, or only IHC&H, or both.

In some embodiments, a sample is prepared with hematoxylin, eosin, and one or more immunohistochemical stains (H&E&IHC), and imaged at multiple wavelengths or color bands. The sample images are converted to optical density units, and then unmixed to obtain component images. The component images are analyzed, and automated image analysis is used to identify segmentation regions and quantify IHC area, strength, or both, within the segmented regions. A synthetic image can also be generated and displayed to an operator. The synthetic image corresponds to contributions from two of the three components (IHC, H, E), while contributions from the third component are substantially absent from the synthetic image.

In some embodiments, the image displayed to the operator corresponds substantially only to an H&E view. In certain embodiments, the view shown to the operator corresponds substantially only to an IHC&H view. In some embodiments, both an H&E view and an IHC&H view are shown to the operator. In certain embodiments, the sample is prepared using two or more IHC stains, and the automated image analysis provides quantitative measures for each.

A wide variety of different types of counterstains can also be applied to samples, in combination with IHC stains. Typically, for example, the counterstains include hematoxylin as a nuclear stain and eosin as a cytoplasm counterstain. Where possible it can be beneficial to use control samples to determine the spectral properties of the IHC stain and of each counterstain.

FIG. 1 is a schematic diagram showing a system 100 for acquiring multiple spectrally resolved images of a sample, for decomposing the sample images to obtain component images, and for generating sample images based on the component images. A light source 102 provides light 122 to light conditioning optics 104. Light 122 can be incoherent light, such as light generated from a filament source for example, or light 122 can be coherent light, such as light generated by a laser. Light 122 can be either continuous-wave (CW) or time-gated (i.e., pulsed) light. Further, light 122 can be provided in a selected portion of the electromagnetic spectrum. For example, light 122 can have a central wavelength and/or a distribution of wavelengths that falls within the ultraviolet, visible, infrared, or other regions of the spectrum.

Light conditioning optics 104 can be configured to transform light 122 in a number of ways. For example, light conditioning optics 104 can spectrally filter light 122 to provide output light in a selected wavelength region of the spectrum. Alternatively, or in addition, light conditioning optics can adjust the spatial distribution of light 122 and the temporal properties of light 122. Incident light 124 is generated from light 122 by the action of the elements of light conditioning optics 104.

Incident light 124 is directed to be incident on sample 108 mounted on illumination stage 106. Stage 106 can provide means to secure sample 108, such as mounting clips or other fastening devices. Alternatively, stage 106 can include a movable track or belt on which a plurality of samples 108 are affixed. A driver mechanism can be configured to move the track in order to successively translate the plurality of samples, one at a time, through an illumination region on stage 106, whereon incident light 124 impinges. Stage 106 can further include translation axes and mechanisms for translating sample 108 relative to a fixed position of illumination stage 106. The translation mechanisms can be manually operated (e.g., threaded rods) or can be automatically movable via electrical actuation (e.g., motorized drivers, piezoelectric actuators).

In response to incident light 124, transmitted light 126 emerges from sample 108. In many embodiments, sample 108 is a tissue sample such as a section of a tissue block, or a fine-needle aspirate, or material from a needle biopsy, or a smear. The sample may be a formalin-fixed paraffin embedded (FFPE) preparation, or it may be a frozen section, or may have been subjected to another preparation protocol according to the needs or interests of the practitioner.

Light collecting optics 110 are positioned to received emitted light 126 from sample 108. Light collecting optics 110 can also be configured to spectrally filter emitted light 126. Further, light collecting optics 110 can be configured to modify the spatial and/or temporal properties of emitted light 126 for particular purposes in embodiments. Light collecting optics 110 transform emitted light 126 into output light 128 which is incident on detector 112.

Detector 112 includes one or more elements such as CCD sensors configured to detect output light 128. In embodiments, detector 112 can be configured to measure the spatial and/or temporal and/or spectral properties of light 128. Detector 112 generates an electrical signal that corresponds to output light 128, and is communicated via electrical communication line 130 to electronic control system 114.

Electronic control system 114 includes a processor 116, a display device 118, and a user interface 120. In addition to receiving signals corresponding to output light 128 detected by detector 112, control system 114 sends electrical signals to detector 112 to adjust various properties of detector 112. For example, if detector 112 includes a CCD sensor, control system 114 can send electrical signals to detector 112 to control the exposure time, active area, gain settings, and other properties of the CCD sensor.

Electronic control system 114 also communicates with light source 102, light conditioning optics 104, illumination stage 106, and light collecting optics 110 via electrical communication lines 132, 134, 136, and 138, respectively. Control system 114 provides electrical signals to each of these elements of system 100 to adjust various properties of the elements. For example, electrical signals provided to light source 102 can be used to adjust the intensity, wavelength, repetition rate, or other properties of light 122. Signals provided to light conditioning optics 104 and light collecting optics 110 can include signals for configuring properties of devices that adjust the spatial properties of light (e.g., spatial light modulators) and for configuring spectral filtering devices, for example. In some embodiments, light conditioning optics 104 may include a spectral dispersion element such as a grating or prism, together with a modulator element that selects one or more wavelengths for passage to the sample 108 while rejecting others; the selection may be driven by control system 114 to effect dynamic selection of wavelengths in coordination with the image acquisition. Signals provided to illumination stage 106 can provide for positioning of sample 108 relative to stage 106 and/or for moving samples into position for illumination on stage 106, for example.

Control system 114 includes a user interface 120 for displaying system properties and parameters, and for displaying captured images of sample 108. User interface 120 is provided in order to facilitate operator interaction with, and control over, system 100. Processor 116 includes a storage device for storing image data captured using detector 112, and also includes computer software that embodies instructions to processor 116 that cause processor 116 to carry out control functions, such as those discussed above for example. Further, the software instructions cause processor 116 to mathematically process the images captured by detector 112 and to carry out the processing steps that will be described in more detail subsequently.

System 100 is configured to acquire multiple spectral images of sample 108. The multiple spectral images may correspond to illumination of sample 108 at a variety of selected wavelengths of light, and detecting an intensity of light either transmitted through or reflected by sample 108. Alternatively, the multiple spectral images may correspond to illumination of sample 108 with light having similar spectral properties, and collecting multiple images of sample 108, each image corresponding to a different wavelength of emitted light 126. Spectral filtering elements in light conditioning optics 104 and light collecting optics 110 are generally used to obtain the spectrally resolved data. Or, the multiple images may correspond to a mixture of these alternatives.

In some embodiments, images of sample 108 can be collected in sequence, with adjustments to the configuration of optical components (e.g., optical filters) between successive captured images. In other embodiments, multiple images can be captured simultaneously using detection systems configured to detect multiple sample views. For example, detection systems can be configured to project different views of the sample corresponding to different illumination or emission wavelengths onto a detector such as a CCD camera, and the multiple views can be captured simultaneously.

In some embodiments, light conditioning optics 104 include an adjustable spectral filter element such as a filter wheel or a liquid crystal spectral filter. The filter element can be configured to provide for illumination of sample 108 using different light wavelength bands. Light source 102 can provide light 122 having a broad distribution of spectral wavelength components. A selected region of this broad wavelength distribution is allowed to pass as incident light 124 by the filter element in light conditioning optics 104, and directed to be incident on sample 108. An image of light 126 transmitted through sample 108 is recorded by detector 112. Subsequently, the wavelength of the filter pass-band in light conditioning optics 104 is changed to provide incident light 124 having a different wavelength, and an image of light 126 transmitted through sample 108 (and corresponding to the new wavelength of incident light 124) is recorded. A similar set of spectrally-resolved images can also be recorded by employing a light source 102 having multiple source elements generating light of different wavelengths, and alternately turning the different source elements on and off to provide incident light 124 having different wavelengths.

In general, both light conditioning optics 104 and light collecting optics 110 may include configurable spectral filter elements. Therefore, spectral resolution can be provided either on the illumination side of sample 108 (e.g., via light conditioning optics 104) or on the imaging side of sample 108 (e.g., via light collecting optics 110), or both. In any case, the result of collecting multiple, spectrally resolved images of sample 108 is an "image stack" where each image in the stack is a two-dimensional image of the sample corresponding to a particular wavelength. Conceptually, the set of images can be visualized as forming a three-dimensional matrix, where two of the matrix dimensions are the spatial length and width of each of the images, and the third matrix dimension is the spectral wavelength to which the image corresponds. For this reason, the set of spectrally resolved images can be referred to as a "spectral cube" of images. As used herein, a "pixel" in such a set of images (or image stack or spectral cube), refers to a common spatial location for each of the images. Accordingly, a pixel in a set of images includes a value associated with each image at the spatial location corresponding to the pixel.

Alternatively, or in addition, other systems and methods for obtaining spectral images which are known in the art can be used, according to the requirements of the sample at hand.

In some embodiments, the Nuance® camera (available from Cambridge Research & Instrumentation, Woburn, Mass.) is connected via a USB interface to a control system 114 consisting of a personal computer having a processor 116 under software instructions that practice the invention as described in detail below. The Nuance® camera is placed at the camera port of a BX61 microscope from Olympus Corporation (Melville, N.Y.). The Nuance system contains a tunable filter located between the sample and the camera, and the overall system images in bright-field mode, using various objective lenses and magnifications according to the goals and the sample at hand. In some embodiments, sample images can be obtained as color pictures from an RGB camera; however, since only three wavelength channels are obtained, this limits the number of stains that can be used to a maximum of three. And, in many cases the results may be of lower accuracy than if one used a system with a higher number of spectral channels, with each channel covering a smaller wavelength range.

In some embodiments, control samples can be used to provide additional information that is useful in analyzing sample images. In particular, for example, control samples can be used to construct a spectral library that includes information about each of the stains that are applied to a sample of interest. Control samples need not be from the same tissue sample as the material to be analyzed, and need not have any unusual properties, excepting that the section used as a control for the IHC stain (or stains) is positive in at least some areas for the target of that stain. For example, if one is seeking to find an IHC marker that binds to regions that express ki67, which is associated with cell proliferation, the control sections used for that stain should have some sites that express ki67, where the reagent will bind.

In general, similar considerations apply to all stains. However, for histological stains like eosin and hematoxylin that readily stain structures in a wide range of tissues, there is usually no need to take special steps to ensure that the control samples will include adequate amounts of the stain.

As an example, one can prepare multiple individual control sample slides, including a first slide prepared only with eosin, a second slide prepared only with only hematoxylin, and a third slide prepared with a single IHC stain of interest. Each slide can then be introduced in turn into a microscope equipped with a multispectral imaging system that takes an image of the sample at a plurality of wavelength bands. In this way, one obtains an image of each stain in isolation, across a particular spectral range. An image can also be obtained of a clear slide with no sample present for use as a reference or baseline for optical density calculations, as will be discussed later.

For the histochemical preparations, conventional staining protocols can be used to apply eosin and hematoxylin to samples. IHC stains can be prepared with a lower concentration of antibody than is normally used. This is because the systems and methods disclosed herein are able to detect IHC stain with greater acuity than a human observer can, and better imagery is often obtained as a result.

In some embodiments, sample images—including images of control slides—can be converted from units of intensity to units of optical density. This conversion can be performed using a reference image obtained with no sample present, according to the following equation:

$$OD = -\text{Log}_{10}(T) = -\text{Log}_{10}(\text{Intensity}_{Sample}/\text{Intensity}_{Reference}) \quad (1)$$

This conversion is performed for the intensity signal at each pixel of interest in the sample. In this way, a partial or complete image can be produced in units of optical density. Optical density calculations can be performed on both images corresponding to control samples, and on images of the actual sample of interest.

From each control sample, one may extract the spectral (or color) distribution that is characteristic of that stain. This can be done by sampling the signal at pixel locations where the stain is observed to be present, which can be done by a computer program that either relies upon operator intervention to select the pixel locations, or that automatically selects locations that are believed to contain stain based on their signal values using image analysis techniques.

When this has been done for each stain, one has a spectral library of stains, and the characteristic spectrum S is known for each stain in the library. Once a spectral library has been determined, it can be used with a variety of samples and need not be reconstructed for each sample. Typically, spectral libraries can be used as long as the same sample preparation protocol and materials are used. When preparation protocols and/or materials change, the spectral library can be reconstructed from new control samples.

In some embodiments, staining protocols can be validated at intervals such as monthly, weekly, or even more often for the case of a high-volume laboratory. Validation can be performed by preparing fresh singly-stained control samples and comparing the spectral distribution of each against the library, to confirm that the expected results are obtained. One metric that can be useful to evaluate the continued suitability of a spectral library is to decompose the signal for each singly stained control sample into its components by spectral unmixing, and to confirm that the estimate for each component other than the applied stain is nearly zero within a predetermined error level.

To obtain component images from the sample spectral images acquired by system 100, the spectral images can be decomposed into contributions from each of the applied stains. In some embodiments, system 100 is configured to perform decomposition using spectral unmixing techniques. Spectral unmixing quantitatively separates contributions in an image that arise from spectrally different sources. For example, a sample may contain three different types of structures, each labeled with a different dye. The three different dyes may each have different absorption spectra. Typically, the individual absorption spectra of the dyes are known before they are used, or they can be measured using control samples, as just described. Images of the specimen under illumination will include, in the most general case, spectral contributions from each of the three dyes, as well as any endogenous absorption contribution(s) from the sample.

Spectral unmixing decomposes images that include contributions from multiple spectral sources into a set of component images (the "unmixed images") that correspond to contributions from each of the spectral entities within the sample. Thus, if the sample includes three different dyes, each specific to a particular structural entity, then an image of the sample can be separated into three unmixed images, each unmixed image reflecting contributions principally from only one of the dyes.

The unmixing procedure essentially corresponds to decomposing an image into a set of spectral eigenstates. In some embodiments, the eigenstates are determined beforehand, as discussed above. In certain embodiments, the eigenstates can sometimes be determined using techniques such as principal component analysis or other techniques. For example, U.S. Pat. No. 7,321,791 describes techniques for doing this in samples that contain two or more stains, and its contents are incorporated herein by reference in their entirety. In any case, once the eigenstates have been identified, an image can be decomposed by calculating a set of values, usually as a coefficient matrix, that corresponds to the relative weighting of each of the eigenstates in the overall image. The contributions of each of the individual eigenstates can then be separated out to yield the unmixed image set.

As an example, a series of two dimensional images having x and y coordinates can be measured for a sample by illuminating the sample at a set of different excitation wavelengths $\lambda_k$ produced by a wavelength-selective illuminator (e.g., system 100). As described above, the two dimensional images can be combined to form a three-dimensional image cube S(x,y,k) where the first two indices of the image cube represent coordinate directions, and the third index is a spectral index corresponding to the setting of the wavelength-selective illuminator element. Assuming, for the sake of simplicity, that each of the images of the sample contains spectral contributions from two different spectral sources $F(\lambda_k)$ and $G(\lambda_k)$, then the values in the three-dimensional image cube S(x,y,k) may be given by $$S(x,y,k)=a(x,y)F(\lambda_k)+b(x,y)G(\lambda_k) \quad (2)$$

where $\lambda_k$ is used to denote a given wavelength (or wavelength band). The functions a(x,y) and b(x,y) describe the spatial abundance of the spectral contributions from the two different spectral sources in the sample.

According to Equation (2), the net signal at any position in the three-dimensional image cube (i.e., at any two-dimensional pixel coordinate, and at a particular illumination wavelength) is the sum of two contributions, weighted by the relative abundance of each. This can be expressed as $$S(\lambda_k)=aF(\lambda_k)+bG(\lambda_k) \quad (3)$$

The functions F and G can be termed the "spectral eigenstates" for the system because they correspond to the pure spectra for the spectral sources in the sample, which are combined in varying proportions to produce the measured spectral images of the sample. Thus, the sample spectrum is a weighted superposition corresponding to separate contributions from the two spectral sources.

When the net signal S is expressed in units of optical density, Equation (3) states that the absorptions of the various stains are additive, and proportional to the amount of stain at a given location, which is essentially a restatement of the Beer-Lambert law for the stains involved. This is usually a very good approximation unless the samples have a high degree of scattering or are unusually densely stained.

If the spectra $F(\lambda_k)$ and $G(\lambda_k)$ are known (or can be deduced), then Equation (3) can be inverted to solve for a and b, provided that spectrum S includes at least two elements (i.e., provided that one has data for at least two wavelengths $\lambda_k$). Equation (3) can be rewritten in matrix form as S=EA, so that $$A=E^{-1}S \quad (4)$$

where A is a column vector with components a and b, and E is a matrix whose columns are the spectral eigenstates, namely [F G].

Using Equation (4), measured spectral images of a sample can be used to calculate contributions to the images arising purely from source F and purely from source G at particular pixel locations. The process can be repeated for each pixel location on a selected image (i.e., throughout the range of values x and y in S) to produce an image of the sample that includes contributions only from source F, and another image of the sample that includes contributions only from source G.

In the above discussion, the number of spectral sources is two (i.e., F and G). In general, however, unmixing techniques are not restricted to any particular number of sources. For example, a sample can generally contain n different spectral sources. If the number of wavelengths at which data is collected is m—that is, k=1 . . . m—then matrix E is an m×n matrix instead of an m×2 matrix, as in the above discussion. The unmixing algorithm can then be employed in the same manner as described above to isolate specific contributions at each pixel location in an image from each of the m spectral eigenstates.

Typically, as discussed above, samples are prepared with at least one IHC stain, eosin (or another nuclear stain), and a counterstain (e.g., hematoxylin). The prepared sample is then placed in a suitable imaging system such as the one described above, and multiple images are obtained corresponding to the sample's transmission at multiple wavelengths or colors. The sample images thus obtained can be converted into units of optical density, according to Equation (1), by dividing the intensity observed when the sample is present with the intensity observed when there is no sample present. Logarithms are then taken; this is conventionally done using base 10 but one may use natural logarithms, or equivalently one may scale the results by any desired factor after a measure is taken that is indicative of optical density.

The sample images are then decomposed to obtain estimates of the amount of each component at each of multiple locations in the image. This decomposition can be done by spectral unmixing of the images after conversion into units of optical density, using a spectral library that is also in units of optical density. The result of this process is a set of component images that correspond to estimates of the amount of each stain present at various locations in the sample. This process can be performed for all pixels in the image so that a complete image of the sample is obtained corresponding to each stain.

These component images can be used in various ways. In some embodiments, the component images are provided to an automated image analysis program to perform region-of-interest determination. In certain embodiments, images are generated based upon the component images and displayed to a technician or pathologist. These synthetic images can have the appearance of a conventional H&E preparation or an IHC&H preparation, for example. In some embodiments, the user can alternate between seeing the same sample presented in different images corresponding to different applied combinations of stains. In certain embodiments, these images can incorporate overlays or indicators that are based on the numerical amount of IHC stain present. Indicators that can be incorporated include, for example, a positivity indicator or heat map, or a pseudocolor overlay where the color is chosen for high visual clarity in distinguishing the IHC signal from the rest of the image. Indicators can be based, for example, on an abundance of the IHC stain at various locations in the sample. Further, indicators can include markers that identify the present of the IHC stain in the sample. The markers can identify regions where the amount of the IHC stain exceeds a predetermined non-zero threshold amount, for example, or regions where the optical density of the IHC stain is larger than a predetermined non-zero optical density.

In some embodiments, regions-of-interest are determined within the acquired spectral images, and then sample images are generated according to contributions from each of the stain components within the regions-of-interest. For example, in certain embodiments, image analysis can be performed using the inForm® software package. This software uses numerical features derived from component images as input features to a neural network classifier, which can be trained by a pathologist or technician to recognize and distinguish between tissue types or structures of interest in a sample. This learn-by-example approach enables one to train the system to find regions-of-interest in a wide range of tissues, for a wide range of tasks.

Overall, image analysis in a learn-by-example system involves three phases. First is a training phase, in which an expert provides input to the system. This person is typically a pathologist, biologist, or technician who is familiar with the tissue involved and the regions-of-interest that are sought. The input is information, typically provided by means of example images, about tissue that corresponds to the regions of interest sought, which may involve assigning tissue into one of several categories such as healthy, inflamed, cancerous, and so on; or identifying tissue structures such as stroma, epithelium, tufts, basal layers, lumens, glands, and so; or locating individual cells of selected types; or combinations of these. Often the expert reviews images of tissue using a computer display, and marks portions of each image using a mouse or other input device, using different colors to indicate different categories of object, structure, or region. Preferably the images represent a range of tissue that spans the range of tissue variability which the system will be asked to classify, and the expert provides training information on tissues within this range.

The second phase is training the computer program based on the information that the expert provided, so that it can perform automated classification. Here the computer program notes what regions in the sample were judged or categorized by the expert, and interrogates the images of the sample to learn one or more of its numerical properties. These properties may include color, brightness, texture, noisiness, morphology, presence of edges or structure, entropy, and other numerical or statistical measures. In general, these properties are termed features, and the software records which values of the features are associated with which regions-of-interest. There are a wide range of possible features that have been devised within the field of computer image analysis. The choice of what particular features to use can be made based on experimental tests of what features lead to good classification accuracy and reliability for a specific purpose.

The features can be generated from a color image of the sample; or from one or more of the images corresponding to a selected wavelength band; or from one or more of the component images corresponding resulting from the decomposition. In some embodiments, the features are generated from one or more component images, including the eosin component image.

The numerical values of the features for a given region are provided to a classifier along with the corresponding expert judgment about that region. The classifier can be a neural network, random forest, or other type of classifier. It then determines a set of weights or boundaries, often iteratively, that are used when it renders its classifications. This process is sometimes called training the classifier. When a classifier is properly trained, it will assign a high proportion of samples to the correct category. The classifier can be tested by supplying some the regions that the expert judged, and comparing the result of the classifier against that of the expert. This can be used as one measure of the classifier training Some classifiers, such as neural networks, can be trained repeatedly, until good classification is obtained; measures such as the comparison against the expert can be used to help determine when the classifier is properly trained.

The third phase is to classify sample images using the trained classifier. This involves calculating one or more features using points or regions in the sample image; providing them to the trained classifier; and generating a judgment about regions-of-interest in the sample. The exact calculation that is performed for this depends on the classifier type, with neural networks, random forests, and distance-classifiers having different algorithms that are known to those skilled in the art of mathematical computation and statistical data modeling.

It is common that these three phases are performed iteratively, and interactively, until reliable performance of a classifier is obtained on a range of samples, after which point the third phase is solely or primarily used. For example, initially an expert may initially provide information on a limited set of samples (first phase), then the expert may train the classifier (second phase), then use the classifier to train other samples that were not included in the training set (third phase). Depending on whether the classifier performs well against the out-of-training samples, the expert may choose to provide supplemental information from these samples or other samples (first phase), and repeat the training (second phase) and classify additional out-of-training samples (third phase) until the results are satisfactory. Once this is demonstrated, routine classification of samples (third phase) does not require practice of the other phases. Methods and systems for image classification are also disclosed, for example, in U.S. Pat. No. 7,555,155, the entire contents of which are incorporated by reference.

The systems and methods disclosed herein provide information about the distribution of eosin in stained samples. Such information is not normally present in systems or methods for analyzing IHC samples, since they omit the eosin stain in order to avoid confounding the observer with visual clutter. However, since the present invention digitally separates the optical signals from the stains, eosin may be applied to the sample without incurring visual clutter; the information it provides can be exploited to gain better region-of-interest performance in automated image analysis, and it also provides further landmarks for visual analysis by a pathologist or technician. Specifically in the case of computerized image analysis, the features used for classification can be generated from the image corresponding to the distribution of eosin stain in the sample, along with other images. The eosin information is especially helpful in cases where cytoplasm texture or presence indicates tissue presence or state, such as in delineating epithelium borders. Further, it improves the quality and reliability of region-of-interest determination in a wide range of sample types. The result is a level of performance that is comparable to a skilled pathologist for finding regions such as tumor, normal epithelial structures, stroma, inflammation, necrosis, vessels, kidney glomerular tufts, pancreas islets, dermal layers, crypts and villi in intestine, and lobular regions, for example.

Because the present invention enables use of information from eosin distribution in samples, which attains a high level of accuracy and reliability in region-of-interest finding, it enables fully automated image processing. In contrast, systems with less reliable region finding typically require the operator either to perform tedious region-drawing, or to review computer-generated regions when processing IHC&H samples.

Sample images can be rendered from one or more of the component images, to produce a view of that sample based on these one or more components. It is not necessary to include all of the component images when doing so, and it is frequently advantageous to exclude one or more component images. In doing so, one can produce views that selectively reveal some stains in the sample while omitting others. This can be useful for reducing visual clutter; or to simulate the appearance that the sample would have if processed with a different stain protocol, such as H&E; or to view individual IHC stains one at a time in a multiplex IHC-stained sample.

In some embodiments, a set of component images is selected, and a color is associated with each image. Rendering an overall image is accomplished by rendering each pixel based on its component contents, to produce an overall sample image from the components. For example, one might choose to render the component images for hematoxylin and for eosin, and choose blue and pink as the colors associated with each stain, respectively. This can produce a good approximation of how the sample would appear if it had been prepared with an H&E stain preparation, even though the actual sample had at least one IHC stain present in addition to the hematoxlyin and eosin. In some embodiments, one might render the component images for hematoxylin and for DAB, and choose blue and brown as the colors for these components. This can produce a good approximation of the visual appearance of an IHC&H sample preparation, though again the actual sample has eosin present, and has a very different appearance from the sample view described.

In certain embodiments, the sample is treated with two IHC preparations, one using Vector red and one using DAB, along with a hematoxlyin stain and an eosin stain. A sample image is produced from the hematoxlyin, Vector red, and DAB component images, using colors of blue, red, and green respectively. DAB is visually brown in color to the human eye, but it can be rendered as green since the view is computer-generated, and the sample image that results has greater visual contrast between the different IHC species than would be attained if DAB were rendered brown.

In some embodiments, more than one sample image is generated and the operator can choose between the generated images, or view them in succession, to provide a combined set of information that is richer than any one image can provide. For example, the operator can be shown an H&E view in which the tissue landmarks are readily evident, and then an IHC&H view of the same sample. It is possible to show the views in alternation, so the operator can quickly locate features of interest in one view, then switch to the other view and see the complementary information it provides.

In certain embodiments, the first image generated is an H&E view; the second image is a first IHC stain with H, and the third image is a second IHC stain with H. Additional images, such as combinations of the IHC stains or a colocalization map of multiple IHC stains, are also possible and can provide valuable information.

One can render the appearance of a pixel from components $A_i$ having associated colors $C_i$, as follows. In this discussion, colors will be described by a triplet of numbers between 0 and 1 that represent the [red, green, blue] values in the RGB colorspace. Thus red is [1, 0, 0], white is [1,1,1] and black is [0,0,0]. Using this notation, one may calculate the color-complement $/C_i$ of a color by subtracting its color triplet from white:

$$/C_i = \text{white} - C_i \tag{5}$$

The complement, in some sense, represents the absorption associated with that color. The complement can be multiplied by the component strength $A_i$ to obtain the color absorption (Abs) at that pixel, arising from that particular stain:

$$Abs_i = /C_i * A_i / K_i \tag{6a}$$

$$Trans_i = \text{white} - Abs_i = \text{white} - /C_i * A_i / K_i \tag{6b}$$

Here, $K_i$ is a scaling factor corresponding to the component strength associated with full color. It can be set to a predetermined value, or it can be set automatically using a rule such as choosing the maximum value of $A_i$ that is present in an image.

From the foregoing equations, one can calculate a pixel's rendered color as:

$$\text{Pixel color} = (Trans_1) * (Trans_2) \ldots * (Tran_N) \tag{7}$$

The asterisk '*' represents multiplying the red elements together; then, repeating for green and blue. Thus the red strength in the rendered pixel color is the product of the red strength in each $Trans_i$ term, and similarly for the green and blue channels. Once the image has been formed by rendering the component signals, it can be further modified by controls that adjust the brightness, contrast, and gamma to suit the preferences of the user.

In addition, the sample image can contain overlays based on the component images, or on regions-of-interest if these have been identified. For example, in some embodiments, the sample image includes indications of the region-of-interest locations. These indications can include outlines, or partially transparent layers, or hash patterns, or any visual device that conveys the desired information. In some embodiments, the regions-of-interest information displays all regions that were found, while in certain embodiments, it shows only regions whose contents meet a criterion, such as the level of an indicator stain being within a chosen range. In some embodiments, it can be useful to indicate all regions-of-interest, but to indicate regions differently according to their contents. For example, regions containing a high (or low) amount of an indicator stain may be displayed in one manner, while regions containing other amounts are displayed differently. In certain embodiments, regions can be displayed differently according to the signal levels of two or more IHC stains that are present, for example to highlight the co-occurrence of both stains.

The sample image can take advantage of other known ways to indicate information in a dense landscape. For example, the image can include a heat map overlay that paints a color grid atop the image that draws a viewer's attention to objects or regions that may be of greater interest, or require review.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

The entire contents of each of the following publications and applications are incorporated by reference herein: U.S. Pat. No. 7,321,791; U.S. Patent Application Publication No. US 2008/0294032; U.S. Pat. No. 7,555,155; U.S. Patent Application Publication No. US 2007/0231784; U.S. Patent Application Publication No. US 2008/0074644; U.S. patent application Ser. No. 12/755,831, filed on Apr. 7, 2010; U.S. Patent Application Publication No. US 2008/0074649; and U.S. Patent Application Publication No. US 2010/0075373.

What is claimed is:

1. A method, comprising:
applying an immunohistochemical stain, eosin, and a counterstain to a sample;
obtaining a plurality of images of the sample, each of the plurality of images corresponding to radiation from the sample in a different wavelength band;
decomposing the plurality of images of the sample to obtain component images corresponding to the immunohistochemical stain, eosin, and the counterstain; and
generating first and second sample images based on the component images derived from the plurality of images, wherein the first sample image comprises contributions from the component images corresponding to the counterstain and to the immunohistochemical stain, and substantially not from the component image corresponding to eosin;

wherein the second sample image comprises contributions from the component images corresponding to the counterstain and to eosin, and substantially not from the component image corresponding to the immunohistochemical stain; and wherein each of the component images that contributes to the first and second sample images corresponds to absorption of radiation by a component of the sample.

2. The method of claim 1, wherein the decomposing comprises spectral unmixing.

3. The method of claim 1, wherein the counterstain comprises hematoxylin.

4. The method of claim 1, further comprising converting intensity values in each of the plurality of images into measurements of optical density.

5. The method of claim 1, the immunohistochemical stain corresponding to a first immunohistochemical stain, and further comprising applying a second immunohistochemical stain to the sample, wherein the decomposing comprises obtaining a component image corresponding to the second immunohistochemical stain.

6. The method of claim 5, further comprising generating a third sample image based on the component images, wherein the third sample image comprises contributions from the counterstain and the second immunohistochemical stain, and substantially not from the first immunohistochemical stain and eosin.

7. A method, comprising:
applying an immunohistochemical stain, eosin, and a counterstain to a sample;
obtaining a plurality of images of the sample, each of the plurality of images corresponding to radiation from the sample in a different wavelength band; and
using an electronic processor to:
(i) decompose the plurality of images of the sample to obtain component images corresponding to the immunohistochemical stain, eosin, and the counterstain;
(ii) analyze one or more of the component images to identify one or more regions of interest in the sample;
(iii) determine an amount of the immunohistochemical stain in one or more of the regions of interest based on at least some of the component images, wherein each of the at least some of the component images corresponds to absorption of radiation by a component of the sample; and
(iv) output one or more indicators corresponding to the determined amount of the immunohistochemical stain.

8. The method of claim 7, further comprising generating one or more component images each comprising a measure of optical density associated with at least one of the immunohistochemical stain, eosin, and the counterstain.

9. The method of claim 7, wherein the decomposing comprises spectral unmixing.

10. The method of claim 7, wherein the counterstain comprises hematoxylin.

11. The method of claim 7, further comprising generating a sample image based on the component images, wherein the sample image comprises contributions from the counterstain and from one of the immunohistochemical stain and eosin, and substantially not from the other of the immunohistochemical stain and eosin.

12. The method of claim 11, wherein the sample image comprises contributions from the immunohistochemical stain and the counterstain, and substantially not from eosin.

13. The method of claim 11, wherein the sample image comprises contributions from eosin and the counterstain, and substantially not from the immunohistochemical stain.

14. The method of claim 12, wherein the sample image further comprises an indicator based on the determined amount of the immunohistochemical stain.

15. The method of claim 14, wherein the indicator corresponds to a measurement of abundance of the immunohistochemical stain in the sample.

16. The method of claim 7, wherein the regions of interest in the sample are identified based on at least a component image corresponding to eosin.

17. The method of claim 7, wherein the regions of interest in the sample are identified based on at least a component image corresponding to the counterstain.

18. A method, comprising:
applying an immunohistochemical stain, eosin, and a counterstain to a sample;
obtaining a plurality of images of the sample, each of the plurality of images corresponding to radiation from the sample in a different wavelength band;
decomposing the plurality of images of the sample to obtain component images corresponding to the immunohistochemical stain, eosin, and the counterstain; and
generating a sample image based on the eosin and counterstain component images,
wherein the sample image comprises an indicator based on information derived from the immunohistochemical component image; and
wherein each of the component images that contributes to the sample image corresponds to absorption of radiation by a component of the sample.

19. The method of claim 18, wherein the indicator comprises markers identifying the presence of the immunohistochemical stain in regions of the sample image.

20. The method of claim 18, wherein the indicator comprises markers identifying regions of the sample image where an amount of the immunohistochemical stain exceeds a predetermined non-zero threshold amount.

21. The method of claim 18, wherein the indicator comprises markers identifying regions of the sample image where an optical density of the immunohistochemical stain is larger than a predetermined non-zero optical density.

22. The method of claim 18, wherein the decomposing comprises spectral unmixing.

23. The method of claim 18, wherein the counterstain comprises hematoxylin.

24. A system, comprising:
a source configured to direct radiation to a sample comprising an immunohistochemical stain, eosin, and a counterstain;
a detector configured to measure radiation emitted from the sample to obtain a plurality of images of the sample, wherein each of the plurality of images corresponds to radiation from the sample in a different wavelength band; and
an electronic processor configured to:
(i) decompose the plurality of images of the sample to obtain component images corresponding to the immunohistochemical stain, eosin, and the counterstain; and
(ii) generate first and second sample images based on the component images derived from the plurality of images, wherein the first sample image comprises contributions from the component images corresponding to the counterstain and to the immunohistochemical stain, and substantially not from the component image corresponding to eosin;

wherein the second sample image comprises contributions from the component images corresponding to the counterstain and to eosin, and substantially not from the component image corresponding to the immunohistochemical stain; and wherein each of the component images that contributes to the first and second sample images corresponds to absorption of radiation by a component of the sample.

25. The system of claim 24, wherein the electronic processor is configured to decompose the plurality of images of the sample by spectrally unmixing the images.

26. A system, comprising:
a source configured to direct radiation to a sample comprising an immunohistochemical stain, eosin, and a counterstain;
a detector configured to measure radiation emitted from the sample to obtain a plurality of images of the sample, wherein each of the plurality of images corresponds to radiation from the sample in a different wavelength band; and
an electronic processor configured to:
(i) decompose the plurality of images of the sample to obtain component images corresponding to the immunohistochemical stain, eosin, and the counterstain;
(ii) analyze one or more of the component images to identify one or more regions of interest in the sample;
(iii) determine an amount of the immunohistochemical stain in one or more of the regions of interest based on at least some of the component images, wherein each of the at least some of the component images corresponds to absorption of radiation by a component of the sample; and
(iv) output one or more indicators corresponding to the determined amount of the immunohistochemical stain.

27. The system of claim 26, wherein the electronic processor is configured to decompose the plurality of images of the sample by spectrally unmixing the images.

28. The system of claim 26, wherein the electronic processor is further configured to generate a sample image based on the component images, and wherein the sample image comprises contributions from the counterstain and from one of the immunohistochemical stain and eosin, and substantially not from the other of the immunohistochemical stain and eosin.

29. The system of claim 28, wherein sample image further comprises an indicator based on the determined amount of the immunohistochemical stain.

30. The system of claim 26, wherein the electronic processor is configured to identify the regions of interest in the sample based on at least a component image corresponding to eosin.

31. The system of claim 26, wherein the electronic processor is configured to identify the regions of interest in the sample based on at least a component image corresponding to the counterstain.

* * * * *